(12) United States Patent
Lendlein et al.

(10) Patent No.: US 8,309,281 B2
(45) Date of Patent: Nov. 13, 2012

(54) PHOTOSENSITIVE POLYMERIC NETWORKS

(75) Inventors: Andreas Lendlein, Berlin (DE); Hong-Yan Jiang, Aachen (DE); Oliver Junger, Mainz (DE)

(73) Assignee: Helmholtz-Zentrum Geesthacht Zentrum feur Material und Kuesten forschung GmbH, Geesthacht (DE)

( * ) Notice: Subject to any disclaimer, the term of this patent is extended or adjusted under 35 U.S.C. 154(b) by 37 days.

(21) Appl. No.: 12/878,559

(22) Filed: Sep. 9, 2010

(65) Prior Publication Data

US 2011/0092609 A1 Apr. 21, 2011

Related U.S. Application Data

(62) Division of application No. 10/541,269, filed as application No. PCT/EP03/14414 on Dec. 17, 2003.

(30) Foreign Application Priority Data

Jan. 8, 2003 (DE) .................... 103 00 271

(51) Int. Cl.
*G03F 7/00* (2006.01)
*G03F 7/004* (2006.01)
*C08L 33/08* (2006.01)

(52) U.S. Cl. .......... 430/19; 430/270.1; 522/68
(58) Field of Classification Search .............. 430/270.1, 430/281.1, 285.1, 288.1, 19
See application file for complete search history.

(56) References Cited

U.S. PATENT DOCUMENTS

| | | | |
|---|---|---|---|
| 3,382,084 A | 5/1968 | Folkins et al. | |
| 3,894,075 A | 7/1975 | Schoen | |
| 4,035,548 A | 7/1977 | Chang et al. | |
| 4,085,092 A | 4/1978 | Chang et al. | |
| 4,857,579 A | 8/1989 | Domeier | |
| 4,923,934 A | 5/1990 | Werner | |
| 5,098,776 A | 3/1992 | Kobayashi et al. | |
| 5,155,199 A | 10/1992 | Hayashi | |
| 5,442,037 A | 8/1995 | Lee et al. | |
| 5,912,257 A | 6/1999 | Prasad et al. | |
| 6,156,842 A | 12/2000 | Hoenig et al. | |
| 6,160,084 A | 12/2000 | Langer et al. | |
| 6,388,043 B1 | 5/2002 | Langer et al. | |
| 6,402,037 B1 | 6/2002 | Prasad et al. | |
| 6,479,222 B1 | 11/2002 | Jones et al. | |
| 6,852,825 B2 | 2/2005 | Lendlein et al. | |
| 2004/0014929 A1 | 1/2004 | Lendlein et al. | |
| 2004/0024143 A1 | 2/2004 | Lendlein | |
| 2005/0118270 A1 | 6/2005 | Moro et al. | |

FOREIGN PATENT DOCUMENTS

| | | |
|---|---|---|
| DE | 689 07 553 T2 | 5/1990 |
| DE | 689 08 081 T2 | 5/1990 |
| DE | 694 26 882 | 4/1996 |
| EP | 0 422 693 | 4/1991 |
| EP | 0 696 605 | 2/1996 |
| FR | 2290452 | 6/1976 |

(Continued)

OTHER PUBLICATIONS

A. Suzuki, et al; Phase transition in polymer gels induced by visible light; Nature Publishing Group; vol. 346; Jul. 26, 1990; pp. 345-347.

(Continued)

*Primary Examiner* — Amanda C. Walke
(74) *Attorney, Agent, or Firm* — VLP Law Group LLP

(57) ABSTRACT

The present invention related to amorphous photosensitive networks. The networks are characterized by good shape memory properties.

14 Claims, 4 Drawing Sheets

Above: photoreaction of cinnamic acid
Below: Reversible Photo crosslinking of cinnamylacylate with UV light
R: Cinnamylacylate ((C₆H₅)-(CH)₄-CO₂-); R': Polymer network;
✕: b-PEG (star shaped, 4 branches).

FOREIGN PATENT DOCUMENTS

| WO | 99/42147 | 8/1999 |
|---|---|---|
| WO | 99/42528 | 8/1999 |
| WO | 01/91822 | 12/2001 |
| WO | 03/084489 | 10/2003 |
| WO | 03/084490 | 10/2003 |
| WO | 03/084491 | 10/2003 |

OTHER PUBLICATIONS

Y. Osada, et al: Soft and Wet Materials; Polymer Gels; Advanced Materials 1998, 10, No. 11; pp. 827-837.

O. Pieroni, et al; Photoresponsive Polmeric Materials; TRIP Vo. 3, No. 9, Sep. 1995; pp. 282-287.

F. M. Andreopoulos, et al; Photoscissable Hydrogel Synthesis via Rapid Photopolymerization of Novel PEG-Based Polymers in the Absence of Phtoinitiators; J. Am. Chem. Soc. 1996, 118, 6235-6240.

M. G. Kodzwa, et al; Photoresponsive control of ion-exchange in leucohydroxide containing hydrogel membranes; Journal of Membrane Science 158 (1999)85-92.

F. M. Andreopoulos, et al; Light-induced tailoring of PEG-hydrogel properties; Biomaterials 19 (1998)1343-1352.

International Search Report for PCT/EP03/14414, published as WO 2004/062706.

Kim, B. K. et al. (1996) "Polyurethanes having shape memory effects," Polymer 37/26:5781-5793.

Lendlein, A. et al . . . , "AB-Polymer Networks Based on Oligo(epsilon-Caprolactone) Segments Showing Shape-memory Properties,"Proc. Natl. Acad. Sci. USA, vol. 98, No. 3, Jan. 2001, pp. 842-847, XP002251532.

Lendlein, A.. et al . . . , "Formgedachtnispolymere,"Angewandte Chemie, vol. 114, No. 12,Jun. 17, 2002, pp. 2138-2162, XP002251533.

Database WPI, Section Ch. Week 199214, Derwent Publication Lt., London, GB; Class A12, AN 1992-109202 XP002251534 & JP 04 050234 A (Asahi Chem Ind Co Ltd.) Feb. 19, 1992.

Patent Abstracts of Japan, vol. 016, No. 213 (C-0942, May 20, 1992) & JP 04 0451416 A (Noevir Co Ltd; Others: 01). Feb. 12, 1992.

Functional principle of a photosensitive network on the macroscopic and molecular level ☐ Photoreactive Group
● Covalent crosslinking point
●● Polymer chain Above: photoreaction of cinnamic acid Below: Reversible Photo crosslinking of cinnamylacylate with UV light R: Cinnamylacylate $((C_6H_5)-(CH)_4-CO_2-)$; R': Polymer network;

✕: b-PEG (star shaped, 4 branches).

Elongation ε of a photosensitive network (Sample 7A) during 3 repetitions of a photomechanical cycle (stress regulated)

PHOTOSENSITIVE POLYMERIC NETWORKS

CROSS REFERENCE TO RELATED APPLICATIONS

This application is a divisional of application Ser. No. 10/541,269, filed May 8, 2006, which is a 371 of PCT/EP2003/014414 filed Dec. 17, 2003, claiming the benefit of German Application No. 103 00 271.5 filed Jan. 8, 2003, all of which are incorporated by reference herein in their entireties.

The present invention relates to photosensitive polymeric networks, photosensitive components, suitable for the preparation of photosensitive polymeric networks as well as methods for programming.

PRIOR ART

Polymeric networks are important building materials in a vast variety of applications, in to which classical network materials, such as metals, ceramics and wood, are no longer sufficient due to their restricted physical properties. Polymeric networks therefore have gained a broad field of application, in particular on the basis of the fact that it is possible to vary the properties of the network materials by a variation of the monomeric units of the polymeric networks.

One particular fascinating class of polymeric networks, which has been developed in the recent years, are the so-called shape memory polymers (in the following shape memory polymers, SMP or SMP-materials), i.e. polymeric networks, which can retain, in addition to their actual, visible shape one or even more shapes in memory, which shapes are recovered only after having been subjected to a specific external stimulus, such as a change in temperature. Due to the possibility to achieve a desired change in shape these materials are of high interest in a vast variety of fields, in which for example a variation in size is desired. This is in particular true for medicinal implants, which shall only reach their final size at the final destination, so that it is possible to introduce these implants using minimal invasive chirurgic processes only. Such materials are for example disclosed in the international patent applications WO-A-99-42528 and WO-A-99-42147.

The majority of shape memory polymers described so far are susceptible to a thermal stimulus. In several fields of application a change of temperature however is not desired, so that a different stimulus, such as light, appears to be more suitable. The use of biocompatible SMPs in living organisms allows for example a temperature increase of only a few degrees above body temperature. Higher temperatures are detrimental for the surrounding tissue. Furthermore most materials are subject to natural changes in temperature. If due to such a natural change in temperature the so-called transfer or trigger temperature of the SMP material is exceeded, the shape memory effect is triggered even though it is not desired to do so.

One possibility for overcoming this drawback is the use of photosensitive SMP materials. Known examples of photosensitive polymers are however mostly gel materials, which may change due to the influence of light their degree of swelling (O. Pieroni, F. Ciardelli, Trends Polym. Sci. 3, 282 (1995); Y. Osada, J.-P. Gong, Adv. Mater, 10, 827 (1996); A. Suzuki, T. Tanaka, Nature 346, 345 (1990). It is for example possible to initiate the sol/gel transfer of a photosensitive gel by means of the influence of light (F. M. Andreopoulos, C. R. Deible, M. T. Stauffer, S. G. Weber, W. R. Wagner, E. J. Beckmann, A. J. Russel, J. Am. Chem. Soc, 118, 6235 (1996).

A further example is the permeability of a membrane made from a photosensitive hydrogel, which can be influenced by light (F. M. Andreopoulos, E. J. Beckmann, A. J. Russel, Biomaterials 19, 1343 (1998).

This process however is only a three-dimensional isotropic reversible change in volume, which is not suitable in order to give rise to defined changes in shape. Gels furthermore are due to their low mechanical stability not sufficient for many fields of application.

The SMP materials disclosed in WO-A-99-42528 and WO-A-99-42147 are prepared from segments. Their partly crystalline morphology gives rise to scattering of light at the surface which prevents a photo reaction within the material. Due to these features such materials cannot be stimulated by means of light.

OBJECT OF THE PRESENT INVENTION

It is therefore the object of the present invention to provide polymeric networks which are able to overcome the drawbacks of the prior art, i.e. which are in particular susceptible to a trigger not associated with temperature. In contrast to hydrogels the materials shall have a high mechanical strength. The polymeric networks shall furthermore enable that it is made possible to design and tailor the properties due to a variation of the composition, so that it is possible to tailor materials having a desired profile of properties.

SHORT DESCRIPTION OF THE INVENTION

The present invention solves this object by providing the photosensitive polymeric network in accordance with claim 1. Preferred embodiments are disclosed in the subclaims. This photosensitive polymeric network in particular is not a hydrogel.

Furthermore the present invention provides photosensitive components which are suitable for the preparation of polymeric amorphous networks, for example in the processes disclosed herein.

Finally, the present invention provides a method for programming of the photosensitive SMP materials. Preferred embodiments are again disclosed in the subclaims.

Further aspects of the present invention are defined in the claims as well as in the following description.

SHORT DESCRIPTION OF THE FIGURES

Figure 4:
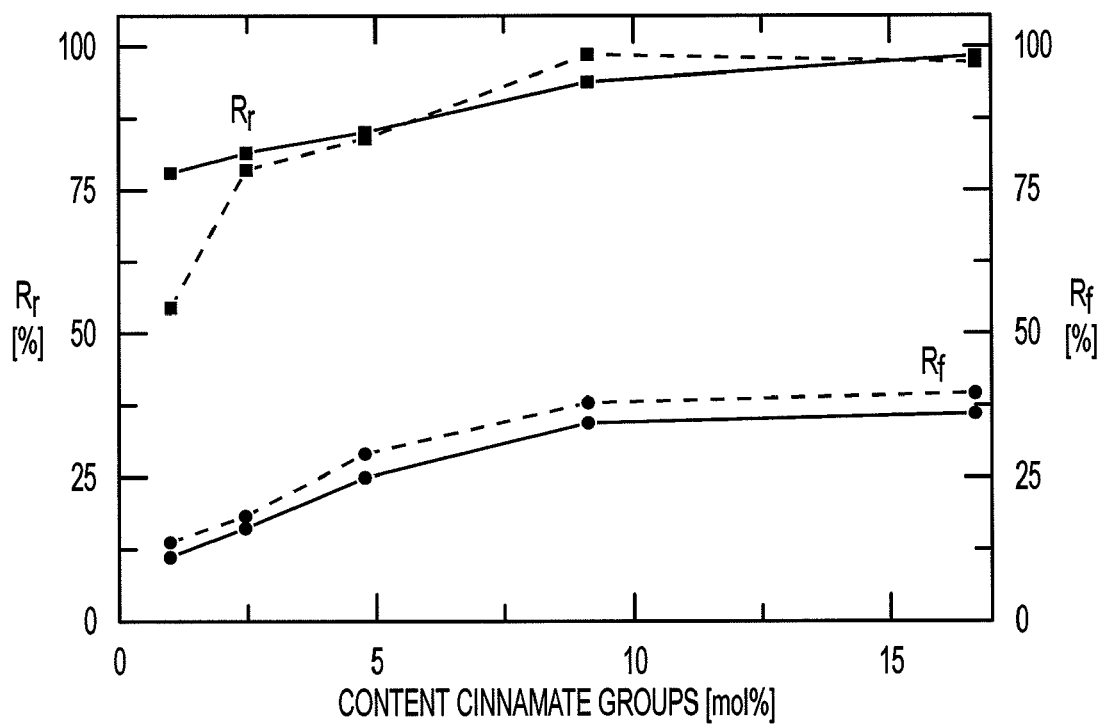

FIG. 4 demonstrates the dependency of the shape memory properties from the content of the photoreactive component.

DETAILED DESCRIPTION OF THE INVENTION

In the following the present invention is described in more detail.

The photosensitive polymeric network in accordance with the present invention comprises a covalently crosslinked polymer (amorphous network), which is provided with photoreactive groups (covalently bound to the amorphous network or mixed in physically), which provide the material light inducible shape memory properties. The polymer main scaffold does not absorb the wavelength acquired for the photoreaction. The network furthermore is substantially amorphous, homogeneous and transparent.

Figure 1:
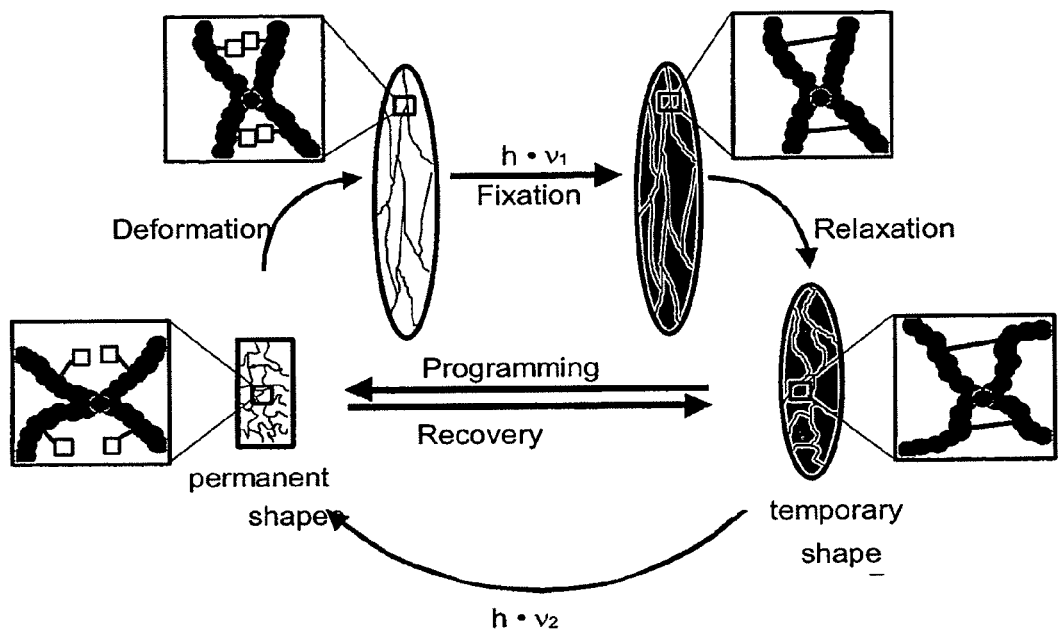
FIG. 1 shows the functional principle of a photosensitive network on macroscopic as well as molecular level.

FIG. 1 shows the functional principle of a photosensitive network on macroscopic and molecular level. Along the main chains of the network, substituents are provided which are equipped at the terminal with a photoreactive group. Upon radiation with UV these groups are able to give rise to covalent bonds. If the material is deformed and irradiated with light of a suitable wavelength $\lambda_1$, the initial network is crosslinked further. Due to this additional crosslinking a temporary fixation of the material in deformed shape is obtained (programming). In view of the fact that the photocrosslinking is reversible, the initial shape of the material can be recovered by means of irradiation with light of another wavelength $\lambda_2$, which disengages the additional crosslinking (recovery). Such a photomechanical cycle can be repeated as often as desired.

In order to provide the desired properties the photosensitive polymeric networks in accordance with the present invention have to be substantially transparent with respect to the irradiation designed for the change in shape. Only then the object mentioned above can be solved. Typically this irradiation is within the UV area, since this enables the prevention of the triggering of the change of shape with light within the visible range, which can hardly be excluded completely in normal life. Furthermore the content of UV irradiation contained in most of the traditional sources of light is not sufficient to trigger the change in shape in the material in accordance with the present invention. Preferably the material of the present invention accordingly is transparent with respect to UV irradiation, in particular within the range of 200 to 400 nm, more preferably within the range of 250 to 350 nm.

Components of the Network

1. Matrix

The basis of the networks is formed by means of a matrix, which, as mentioned above, is transparent with respect to the irradiation designed for the triggering of the change in shape, i.e. preferably a UV transparent matrix. Furthermore this matrix should show a certain degree of elasticity and flexibility (elastomeric properties). Furthermore it is required that the matrix is amorphous. Furthermore it is important that the matrix is crosslinked, in order to provide a certain degree of mechanical stability, as well as the desired shape memory properties in accordance with the present invention. In principle all polymerizable compounds are employable in accordance with the present invention, provided that they are suitable for the preparation of a matrix as designated above. Preferably these compounds should be polymerizable in bulk.

It is preferred in accordance with the present invention when the basis of the network of the present invention is a matrix on the basis of low molecular acrylates and methacrylates, which may be polymerised by means of a radical mechanism, in particular $C_1$-$C_6$-(meth)acrylates and hydroxy derivatives thereof, wherein hydroxyethylacrylate, hydroxypropyl methacrylate, hydroxypropyl acrylate, poly(ethylene glycol)methacrylate and n-butylacrylate are preferred, in particular n-butylacrylate and hydroxyethylmethacrylate.

N-butylacrylate, which is preferred as matrix component, has the advantage that the homopolymer possesses a low glass transition temperature of −55° C., so that one may expect elastic properties for the networks on the basis of this component. A comonomer, in particular hydroxyethylmethacrylate, serves optionally for tailoring the thermal and mechanical properties. These two compounds can be polymerised in any ratio, wherein, if hydroxyethylmethacrylate (HEMA) is present, n-butylacrylate should represent the major part. Preferred mol ratios of n-butylacrylate to HEMA are within the range of from 10:0.1 to 10:5, preferably 10:1 to 10:3 in particular about 10:2.

2. Crosslinking Agents

In addition to the material for the matrix the polymeric network in accordance with the present invention also comprises a component, responsible for the crosslinking of the matrix. The chemical nature of this component depends obviously from the nature of the matrix materials. Again it is possible to use a broad variety of compounds, adjusted to the matrix materials.

For the preferred networks on the basis of the acrylate materials described above as preferred embodiments, suitable crosslinking agents are bifunctional acrylate compounds, which do have a suitable reactivity with the starting material for the matrix, so that they can be reacted together. Such crosslinking agents comprise short chain bifunctional crosslinking agents, such as ethylene diacrylate, low molecular weight bi- or polyfunctional crosslinking agents, oligomeric, linear diacrylate crosslinking agents, such as poly(oxyethylene)diacrylate or poly(propylene)diacrylate and branched oligomers or polymers having acrylate terminals.

As crosslinking agent it is preferred to use a dimethacrylate, in particular poly(propylene glycol)dimethacrylate, having a molecular weight of from 300 to 1,000 g/mol, preferably about 560 g/mol. The crosslinking agent is used in relatively low concentrations of about 0.3 to 3 mol %, based on the total amount of material to be polymerised to the network, in order to obtain elastic networks. Higher amounts of crosslinking agents do give rise to less elastic materials or even brittle materials.

In accordance with the present invention the introduction of the crosslinking agents in the network occurs by simple mixing of the crosslinking agent with the starting materials for the matrix, followed by polymerisation, preferable in bulk, using suitable initiators.

3. Photoreactive Component

As further component the network in accordance with the present invention comprises a photoreactive component (group), which is also responsible for the triggering of a change in shape which is controllable. This photoreactive group is a unit, able to undergo a reversible reaction (with a second photoreactive group) by means of stimulation with suitable light irradiation, preferably UV irradiation, enabling the formation or the dissociation of covalent bond. Preferred photoreactive groups are photoreactive groups able to undergo a reversible photodimerization.

The photoreactive components may, upon suitable functionalization, either be directly copolymerised using a radical reaction with the above-mentioned monomers or may form the inter-penetrating part of an inter-penetrating network (IPN).

Suitable photoreactive components are photoreactive components which do have the properties mentioned above and which can either be copolymerised into the network (for example in an acrylate containing network by means of introducing the photo active group into an acrylate monomer or acrylate oligomer) or which can be introduced into the already established network by means of swelling procedures or the like, for example in the form of suitably functionalised polymers or oligomers.

As photoreactive component it is preferred to use in the photosensitive network in accordance with the present invention cinnamic acid esters (cinnamates, CA) and cinnamyl acid acyl esters (cinnamylacylates, CAA).

It is known that cinnamic acid and its derivatives dimerize under the influence of UV light of about 300 nm forming a cyclobutane. These dimmers can be cleaved again, when irradiated with UV light of shorter wavelength of about 240 nm. The absorption maxima may be changed for example by substituents at the phenyl ring, however, the absorption maxima always remain within the UV area. Further derivatives which may show photo dimerization are 1,3-diphenyl-2-propene-1-one (chalkon), cinnamylacyl acid, 4-methylcoumarin, various ortho-substituted cinnamic acids, cinnamyloxysilanes (silylether of cinnamic alcohol).

Figure 2:
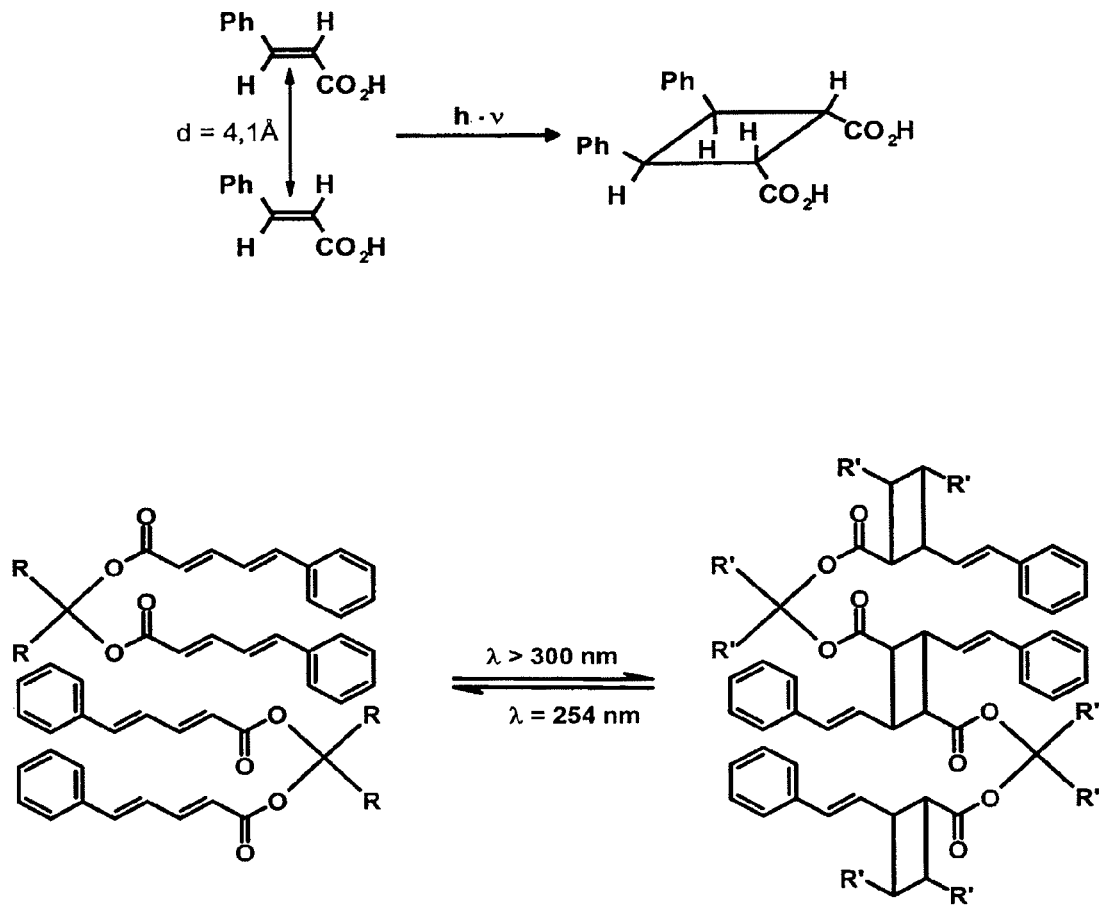
FIG. 2 shows the photoreaction of cinnamic acid and of a cinnamylacylate.

The photo dimerisation of cinnamic acid and similar derivatives is a [2+2] cyclo addition of the double bonds giving rise to a cyclobutane derivative. The I- as well as the Z-isomers are able to show this reaction. Upon irradiation the E/Z-isomerization occurs concurrently and in competition with the cyclo addition. In the crystalline state the E/Z-isomerization is however inhibited. Due to the different possibilities of arrangement of the isomers 11 theoretical different stereo isomer products are possible (truxilic acids, truxinic acids). The distance required for the reaction (between double bonds of two cinnamic groups) is about 4 Å. FIG. 2 shows the photoreaction of cinnamic acid and or a cinnamylacylate.

The introduction of the photoreactive component into the network in accordance with the present invention occurs, as disclosed above, using two alternatives. On the one hand it is possible to copolymerize the photoreactive group (component) into the matrix of the network, so that the network as such is photoreactive. This simplifies in a certain way the method for preparation, since after one single polymerisation the polymeric photosensitive network can be obtained. Further optional reaction steps relate then only to purification steps or steps for the introduction of further optional components. At the same time this enables to tailor in a simple way the properties of the network in accordance with the present invention, since substantially the polymerization mixture already defines these properties. The second alternative is defined by the fact that not the network as such is provided with the photoreactive group but that the photoreactive group is introduced by means of physical processes into the network matrix. A typical example thereof is the preparation of an IPN using a crosslinked polymer matrix (which can be as described above) together with a suitably functionalised second polymer or oligomer, which provides the photoreactive group and which is able to penetrate the network. An advantage of this alternative is the fact that the preparation of the polymeric network matrix is not subjected to severe limitations, since the sensitive and even sometimes detrimental photoreactive group is not present during the preparation of the network matrix. For example in this case the network matrix can polymerised by means of UV initiation, which is not possible with the first alternative, since in this case the photoreactive groups of the photoreactive component might interfere with the polymerisation.

In order to prove the photoreaction (cyclo addition) different spectroscopic methods can be employed. By means of UV spectroscopy it is possible to observe the increase of the absorption maximum at 275 nm due to the loss of conjugation of the π-electrons of the benzol ring with the alkene-carbonyl-group.

3.1 Copolymerization of the Photoreactive Component

One possibility for the introduction of the photoreactive component into the network is the coupling of the photoreactive group to the starting material of the network matrix. With respect to the preferred networks on the basis of acrylates it is for example possible to esterify the corresponding cinnamic acid chlorides or cinnamylacyl acid chlorides with hydroxyalkylacrylates or hydroxyalkylmethacrylates. Thereby one obtains photoreactive esters, which can be easily copolymerised with other monomers using a radical reaction. Suitable hydroxyacrylates and hydroxymethacrylates for esterification with cinnamic acid (CA) or cinnamylacyl acid (CAA) are hydroxyethylmethacrylate (HEMA), hydroxyethylacrylate (HEA), hydroxypropylmethacrylate (HPMA), hydroxypropylacrylate (HPA), polyethylene glycol)methacrylate (PEGMA). Esterification occurs under conditions which are known to the skilled person from the prior art (method according to Schotten-Baumann, the hydroxyalkylacrylate or the hydroxymethacrylate is dissolved in diethylether and is reacted first with a cinnamic acid chloride and then with triethylamine).

The radical polymerisation of the above named components in order to produce the network preferably occurs in bulk, using a thermolabile initiator. Suitable initiators are peroxides, such as benzoylperoxide, di-tert-butylperoxide, as well as azo compounds, such as azobisisobutyronitrile (AiBN). Preferable an AiBN is used in concentrations of 0.1 to 1 wt %.

The amount of photoreactive component usually is from 1 to 30 mol %, on the basis of the total mixture of 1. to 3., preferable 2 to 20 mol %, more preferably 4 to 12 mol % e.

The copolymerisation gives rise to a random (statistical) distribution of the photoreactive component within the polymeric network, as was demonstrated by means of spectroscopic determination. This ensures the shape memory properties, since only an even distribution of the photoreactive component within the total network establishes uniform, reproducible and reliable shape memory properties.

3.2 Subsequent Loading (Physical Mixing)

A further possibility to provide a network with photoreactive groups is the subsequent physical loading of non-functionalized networks. Loading of a network can be carried out by placing the network in a solution of the photoreactive component in order to swell the network, followed by drying. The photoreactive component penetrates the entire network. If the loaded network is irradiated subsequently with UV light the photoreactive group dimerizes under formation of a reversible network within the permanent network. An interpenetrating network (IPN) is produced.

The non-functionalized network of this embodiment corresponds preferably to the amorphous network, described above which comprises a matrix component and a crosslinking agent. The above-mentioned preferred embodiments are also preferred with respect to the present embodiment.

In order to provide a reversible network at all it is required that the photoreactive component comprises at least three photo crosslinkable groups per molecule. For the loading of the permanent networks therefore star shaped, branched polymers or oligomers are suitable, or comb like or rod like graft-polymers or graft-oligomers are suitable. Preferred is a star shaped macro monomer comprising a photoreactive group at each chain terminal (branch). The branches consist preferably of alkylene glycol units.

The macro monomer can be produced from star shaped molecules having terminal OH-groups, which are esterified with the above-mentioned photoreactive acid chlorides. Preferably a 4-branched polyethylene glycol having a molecular weight of 400 to 1000 g/mol preferably about 560 g/mol is used, which can be obtained from commercial sources. The molecular weight and the number of branches however, are not essential. However, at least three branches are required. Esterification occurs under the conditions known from literature.

The loading of the network with the photoreactive component occurs by swelling the network in a solution of a photoreactive component. For the preferred network on the basis of acrylates, loaded with the preferred four branch star shaped photoreactive components, the loading amounts preferably to 5 to 45 wt %, based on the total mixture, more preferred 15 to 35 wt % and in particular 25 to 25 wt %, most preferably about 30 wt %.

Also in the IPNs, which are preferred in accordance with the present invention, the photoreactive component is present within the network in a substantially even distribution, which ensures, as disclosed above, the shape memory properties.

Photosensitive Networks

Simple Networks

By means of radical polymerisation of a cinnamic acid ester, as described above, with acrylates or methacrylates, as mentioned above, photoreactive networks can be prepared, which will be demonstrated under reference of two network series. For the first series a cinnamic acid ester was copolymerised with two components (n-butylacrylate and poly(propylene glycol) dimethacrylate), whereas in the second series the copolymerization occurred with three components (additionally hydroxyethylmethylacrylate HEMA). The concentration of the cinnamic acid ester was varied within each series. The content of photoreactive component in the mixtures amounted to between 0.075 and 1.27 mmol/g.

The values for the gel content of the obtained networks, i.e. the content of components which cannot be extracted, are often above 90%, in most cases even above 95%, which corresponds to high turnovers. It therefore can be assumed that a monomer mixture and the corresponding network do show identical composition.

IPN

Networks suitable for physical loading with photosensitive components (macro monomer) preferably consist of n-butylacrylate and poly(propylene glycol)dimethacrylate. The networks are swollen in a solution of the macro monomer in THF and dried subsequently.

The degree of loading can be varied by adjusting the concentration of the solution. After drying of the samples a weight increase of for example 30% can be detected, with a solution comprising 10 wt % of macro monomer. This corresponds to a content of photoreactive groups within the network of 0.32 mmol/g (0.32 mmol/g×85% functionalization of the terminal group=0.27 mmol/g).

The photosensitive networks in accordance with the present invention are characterized by the following properties.

All networks are transparent, which signifies a homogeneous, amorphous morphology. An exception are networks 10A-C, which are slightly opaque.

The networks are characterized by a low glass transition temperature. For the networks of the series without HEMA these temperatures are between −46.1 and −10.9° C. (DSC). With HEMA the temperature lies between −11.9 and 16.1° C. As a tendency it can be said that the glass transition temperature increases with increasing contents of photoreactive components.

Above the glass transition temperature the networks are elastic. At room temperature the stress at rupture of the networks without HEMA amounts to 20 to 45%, whereas the networks with HEMA show values of up to 60%. E-modulus increases with increasing amounts of photoreactive comonomer within the network to values of up to 4.2 MPa (networks without HEMA) and 120 MPa (with HEMA) respectively, i.e. elasticity decreases. The inter-penetrating networks can be elongated by 100% without rupture.

By means of the photoreaction the mechanical properties of the materials change. The UV irradiation with $\lambda_1$ gives rise to a covalent crosslinking of the photoreactive groups and may increase the E-modulus by 18% (Example IPN). With the irradiation with UV light of the other characteristic wavelength $\lambda_2$ the crosslinkage is dissolved and E-modulus decreases again.

The high elasticity of the networks prior to irradiation enables a simple deformation of the material for programming of a temporary shape. The amorphous networks of the present invention are good SMP materials having high degree of recovery, i.e. the original shape is recovered with a high accuracy even after several cycles of shape change. Expressed in percentage the recovery rates amount usually to more than 90%. Also it can be said that no detrimental loss of mechanical properties occurs.

The shape memory properties of the materials of the present invention are defined in the following.

Shape memory polymers in accordance with the present invention are materials, which are, due to their chemical-physical structure, able to undergo desired shape changes. These materials posses, in addition to their principle permanent shape, a further shape which can be impressed temporarily. Such materials are characterized by two features. They comprise the so-called photoreactive group, which can initiate a light stimulated transfer. Furthermore, these materials comprise covalent crosslinking points, which are responsible for the so-called permanent shape. This permanent shape is characterized by the three-dimensional structure of a network. The crosslinking points present in the network in accordance with the present invention are of covalent nature and are obtained in the preferred embodiments of the present invention by means of polymerisation of acrylate terminal groups or methacrylate terminal groups. The photoreactive groups, which trigger the light induced transfer (shape change), are in the present invention, with respect to the preferred embodiments, the cinnamate groups or the cinnamyl acyl groups.

A photo mechanical cycle comprises the following steps: Elongation of the sample, irradiation with $\lambda_1$ (fixation, programming), relaxation of the sample, irradiation with $\lambda_2$ (recovery). By suitable stress strain experiments the shape memory effect can be demonstrated. As example for such stress strain measurements FIG. 3 shows the mechanical behaviour of a photosensitive network during three photomechanical cycles.

Figure 3:
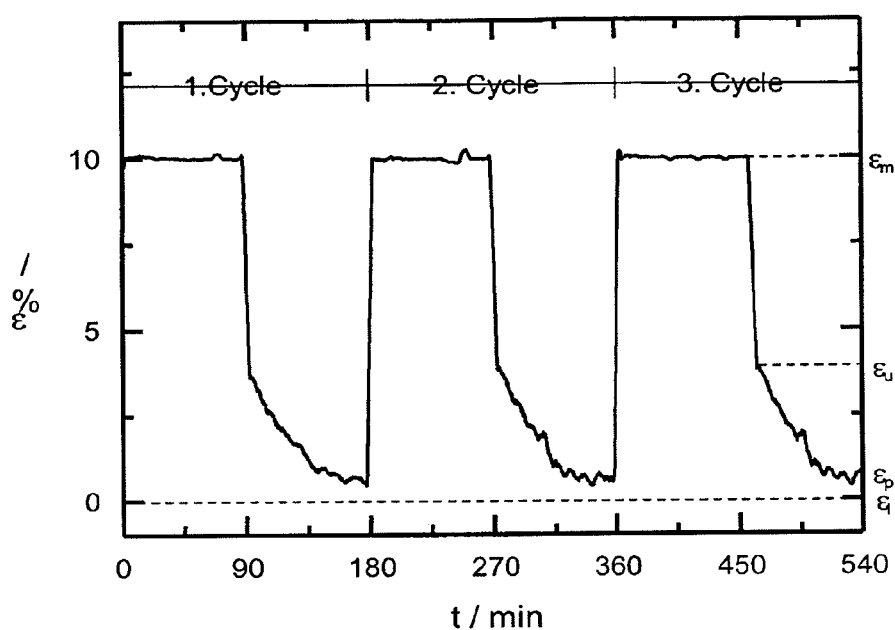
FIG. 3 shows the mechanical properties of a photosensitive network during a cyclic photomechanical experiment.

In FIG. 3 a SMP foil was elongated by 10% (from $\epsilon_l$ to $\epsilon_m$) and irradiated for 90 minutes with $\lambda_1$>250 nm (45 minutes per side). The accuracy with which the temporary shape can be fixed is designated shape fixation $R_f$. The clamps were then brought to the initial distance ($\epsilon_u$) and the (bended foil) was irradiated in this stress relieved status for 90 minutes with $\lambda_2$<250 nm. During this irradiation the foil contracts again (shape memory effect), whereby however in the first cycle not exactly the original length is obtained but a small residual elongation remains within the material ($\epsilon_p$) (Equilibration during the first cycles). The accuracy with which the initial shape is recovered is designated recovery ratio $R_r$.

$R_f$ and $R_r$ can be calculated as follows:

$$R_f = \epsilon_u/\epsilon_m \times 100 \quad (a)$$

and $$R_r(N) = (\epsilon_m - \epsilon_p(N))/\epsilon_m - \epsilon_p(N-1) \times 100 \quad (b)$$

with N=number of cycle.

Irradiation of the elongated sample can occur either under length regulation (constant sample length) or stress regulated (constant stress). If elongation is kept constant during irradiation, the stress increases. With constant stress it is usually possible to detect a contraction of the sample. FIG. 4 shows that the selection of the method has only a small influence on the shape memory properties. The shape memory properties depend from the concentration of the photoreactive group in the network, as can be derived from FIG. 4. $R_r$ and $R_f$ (the $5^{th}$ cycle was taken as the relevant cycle) reach at a concentration of about 18% a limit.

The photosensitive polymeric networks in accordance with the present invention are characterized in that for the first time shape memory materials have been provided which can be triggered using a stimulus being different from temperature. Thereby the present invention opens a new field of shape memory materials and opens new options for the use of such materials in application areas in which temperature triggered shape memory materials cannot be used. The preferred networks in accordance with the present invention furthermore can be triggered with UV light of a narrow wavelength area, an area posing no problems for most of the applications, since suitable sources for irradiation are present and since furthermore this wavelength area is of no harm for other materials.

The amorphous network in accordance with the present invention may comprise, in addition to the above discussed essential components, further compounds, as long as the function of the network is not affected. Such additional materials may be for example coloring agents, fillers or additional polymer materials, which are used for various purposes. In particular the amorphous network of the present invention to be used for medicinal purposes may comprise medicinal active principles and diagnostic agents such as contrast agents. These can be introduced into the network in a usual manner.

The following examples illustrate further the present invention.

Preparation of Star Shaped Photosensitive Macro Monomers

Star shaped polyethylene glycol with 4 branches (molecular weight 2000 g/mol) is dissolved in dry THF and triethylamine. To this solution slowly a solution of cinnamylidene acetyl chloride dissolved in dry THF is added. The reaction mixture is stirred for 12 hours at room temperature and then for 3 days at 50° C. Precipitated salts are filtered off, the filtrate is concentrated and the obtained product is washed with diethyl ether. H-NMR measurements show a turnover of 85%. UV spectroscopy shows that the macro monomer has an absorption maximum at 310 nm prior to photoreaction and an absorption maximum of 254 nm after photoreaction.

Preparation of Networks 10 mmol n-butylacrylate (BA), a cinnamic acid ester (0.1-3 mmol) and optionally 2 mmol hydroxyethlmethacrylate (HEMA) are mixed in a glass flask. To this mixture 1 mol % AiNB and 0.3 mol % poly(propylene glycol)dimethacrylate (Mn=560) are added. The mixture is introduced with a syringe into a mould formed by two silated glass plates, provided therebetween a teflon ring having a thickness of 0.5 mm. Polymerization of the mixture occurs during 18 hours at 80° C.

The shape in which the crosslinking occurs corresponds to the permanent shape. The mixture can also be crosslinked in any other desired shape.

After the polymerisation the network is removed from the mould and covered with 150 ml hexane. Thereafter portions of chloroform are added. This solvent mixture is exchanged over the next 24 hours several times in order to removed low molecular compounds and non-crosslinked components. Finally, the network is cleaned with hexane and dried in a vacuum at 30° overnight. The weight of the extracted sample, relative to the initial weight corresponds to the gel content. The following two tables show the amounts of the monomers used as well as the swelling of the networks in chloroform and the gel content of the networks.

| | Monomer content of mixture (mmol) | | | | | | | |
|---|---|---|---|---|---|---|---|---|
| Nr. | BA | HEMA-CA | HEA-CA | HPMA-CA | HPA-CA | PEGMA-CA | Q (%) | G (%) |
| 1A | 10 | 0.25 | — | — | — | — | 720 | 97.2 |
| 1B | 10 | 0.5 | — | — | — | — | 550 | 94.9 |
| 1C | 10 | 1 | — | — | — | — | 400 | 91.6 |
| 2A | 10 | — | 0.1 | — | — | — | 620 | 89.0 |
| 2B | 10 | — | 0.25 | — | — | — | 900 | 96.2 |
| 2C | 10 | — | 0.5 | — | — | — | 680 | 95.7 |
| 2D | 10 | — | 1 | — | — | — | 1320 | 96.5 |
| 2E | 10 | — | 2 | — | — | — | 1320 | 96.5 |
| 3A | 10 | — | — | 0.25 | — | — | 950 | 98.7 |
| 3B | 10 | — | — | 0.5 | — | — | 650 | 93.4 |
| 3C | 10 | — | — | 1 | — | — | 450 | 98.4 |
| 4A | 10 | — | — | — | 0.25 | — | 830 | 95.9 |
| 4B | 10 | — | — | — | 0.5 | — | 700 | 98.1 |
| 4C | 10 | — | — | — | 1 | — | 550 | 94.3 |
| 5A | 10 | — | — | — | — | 0.25 | 600 | 98.2 |
| 5B | 10 | — | — | — | — | 0.5 | 550 | 97.3 |
| 5C | 10 | — | — | — | — | 1 | 530 | 92.4 |

In a further series an amount of 2 mmol hydroxyethylmethacrylate (HEMA) is added to the binary polymer system, in view of the fact that this comonomer enables a further possibility to control the mechanical properties of the polymer networks.

| | Monomer content of mixture (mmol) | | | | | | | | |
|---|---|---|---|---|---|---|---|---|---|
| Nr. | BA | HEMA | HEMA-CA | HEA-CA | HPMA-CA | HPA-CA | PEGMA-CA | Q (%) | G (%) |
| 6A | 10 | 2 | 1 | — | — | — | — | 370 | 95.5 |
| 6B | 10 | 2 | 2 | — | — | — | — | 350 | 99.2 |
| 6C | 10 | 2 | 3 | — | — | — | — | 420 | 96.8 |
| 7A | 10 | 2 | — | 1 | — | — | — | 390 | 98.5 |
| 7B | 10 | 2 | — | 2 | — | — | — | 300 | 92.8 |
| 7C | 10 | 2 | — | 3 | — | — | — | 250 | 96.4 |
| 8A | 10 | 2 | — | — | 1 | — | — | 240 | 94.4 |
| 8B | 10 | 2 | — | — | 2 | — | — | 310 | 92.3 |
| 8C | 10 | 2 | — | — | 3 | — | — | 310 | 92.9 |
| 9A | 10 | 2 | — | — | — | 1 | — | 450 | 94.7 |
| 9B | 10 | 2 | — | — | — | 2 | — | 360 | 82.7 |
| 9C | 10 | 2 | — | — | — | 3 | — | 380 | 80.2 |
| 10A | 10 | 2 | — | — | — | — | 1 | 1300 | 83.4 |

-continued

| Nr. | BA | HEMA | HEMA-CA | HEA-CA | HPMA-CA | HPA-CA | PEGMA-CA | Q (%) | G (%) |
|---|---|---|---|---|---|---|---|---|---|
| 10B | 10 | 2 | — | — | — | — | 2 | 1450 | 83.8 |
| 10C | 10 | 2 | — | — | — | — | 3 | 2150 | 84.8 |

Preparation of Inter-Penetrating Networks IPN n-butylacrylate is crosslinked with 3 wt % (0.6 mol %) poly(propylene glycol)dimethacrylate (molecular weight 560 g/mol) in the presence of 0.1 wt % AiBN, as described above. The obtained film is swollen in THF in order to remove unreacted monomer, followed by drying. Thereafter the film is placed into a solution of the star shaped photoreactive macro monomer in THF (10 wt %) in order to swell the network, followed by drying. The loading of the network with the photoreactive component amounts thereafter to about 30 wt %. The polymeric amorphous networks are furthermore evaluated with respect to their thermal and mechanical properties. The results of these evaluations are summarized in the following table.

| Nr. | $T_g$ (° C.) | E-Modulus E at RT (MPa) | Stress at break $\sigma_r$ at RT (MPa) | Elongation at break $\epsilon_r$ at RT (%) |
|---|---|---|---|---|
| 1A | −40.8 | 0.54 | 0.24 | 45 |
| 1B | −34.5 | 1.10 | 0.21 | 15 |
| 1C | −21.2 | 1.77 | 0.24 | 10 |
| 2A | −46.1 | 0.29 | 1.00 | 20 |
| 2B | −40.3 | 0.22 | 0.15 | 20 |
| 2C | −35.6 | 0.94 | 0.18 | 20 |
| 2D | −19.9 | 1.69 | 0.42 | 20 |
| 2E | −10.9 | 4.22 | 0.12 | 35 |
| 3A | −30.6 | 0.56 | 0.15 | 30 |
| 3B | −22.8 | 0.90 | 0.31 | 35 |
| 3C | −18.6 | 2.39 | 0.44 | 25 |
| 4A | −40.5 | 0.54 | 0.18 | 35 |
| 4B | −34.9 | 1.04 | 0.24 | 25 |
| 4C | −24.9 | 1.88 | 0.35 | 25 |
| 5A | −38.8 | 0.36 | 0.08 | 20 |
| 5B | −36.5 | 1.44 | 0.10 | 15 |
| 5C | −29.6 | 1.41 | 0.22 | 6 |
| 6A | −10.0 | 1.80 | 0.34 | 25 |
| 6B | 2.2 | 11.52 | 2.48 | 35 |
| 6C | 16.1 | 120.69 | 9.66 | 15 |
| 7A | −11.4 | 2.67 | 0.51 | 25 |
| 7B | 7.3 | 9.71 | 2.26 | 30 |
| 7C | 12.6 | 39.78 | 5.28 | 25 |
| 8A | −11.9 | 2.35 | 0.83 | 45 |
| 8B | 6.6 | 25.02 | 5.17 | 50 |
| 8C | 10.4 | 139.9 | 13.06 | 15 |
| 9A | 3.5 | 1.53 | 0.53 | 50 |
| 9B | 8.5 | 14.04 | 4.55 | 60 |
| 9C | 13.9 | 32.42 | 6.42 | 50 |
| 10A | −27.4 25.7 | 1.40 | 0.29 | 30 |
| 10B | −23.6 52.8 | 2.41 | 0.67 | 25 |
| 10C | −20.0 56.6 | 4.74 | 0.96 | 25 |
| 11 * | −46.5 | 0.15 | >1.60 | >2000 |
| 12 ** prior to irradiation | −45.0 | 0.17 | 1.0-1.5 | 300-500 |
| 12 ** after irradiation | −40.0 | 0.20 | 0.5-0.9 | 30-100 |

\* Network of n-butylacrylate, 0.3 mol % crosslinking agent, without photoreactive component
\*\* IPN; 0.6 mol % crosslinking agent, physically loaded with photoreactive component The shape memory properties were evaluated in cyclic photo mechanical experiments. For these experiments dumb bell-shape samples, prepared by punching having a thickness of 0.5 mm and a length of 10 mm and a width of 3 mm were used.

Optionally the material is pretreated prior to the start of the photomechanical cycles by irradiation with $\lambda_2$, in order to cleave cyclobutane rings which may be present in the material, so that preferably all photoreactive groups are present in their monomeric form. The elongation of the samples occurs at a rate of 10 mm/min. In order to fix the temporary shape the samples are elongated by 30% and irradiated at constant stress. In order to trigger the shape memory effect the samples were irradiated again without external stress.

Irradiation of the samples occurred by means of a UV lamp. With the use of a filter the right wavelength area is selected.

Normal networks with CA: $\lambda_1$=>250 nm, $\lambda_2$=<250 nm
IPN with CAA: $\lambda_1$=>300 nm; $\lambda_2$=254 nm The distance to the sample was 10 cm when a lamp with 200 watt was employed (>300 nm), or 3 cm, when using a 4 watt lamp (254 nm), or 10 cm, using a 40 watt lamp (> and <250 nm).

The optimum duration of irradiation depends for example from the distance of the lamp to the sample and from the light intensity. For normal networks a duration of irradiation of 30 minutes per side is sufficient in order to obtain the maximum values for $R_f$ and $R_r$. In the case of IPNs a maximum value for $R_f$ of 21% is obtained after 4 hours of irradiation.

These experiments demonstrate the superior properties of the amorphous networks of the present invention. The networks are characterized by providing good values for the total recovery after 5 cycles, which is a characterizing property for SMP properties. This is shown in the following table. Materials of the prior art show often values of less than 80%.

Due to the simple building blocks of the networks in accordance with the present invention it is furthermore secured that the synthesis is not too complicated. By varying the composition, as demonstrated above, polymeric materials can be tailored which are characterized by desired combinations of properties.

The materials in accordance with the present invention are in particular suitable for use in the medicinal field, as implants, for the target designed stimuli sensitive drug release, as argumentation materials for ligaments or as replacement materials for discs. Furthermore the amorphous networks are above the glass transition temperature transparent, which is of further advantage for certain fields of application.

The invention claimed is:

1. A photoreactive component, comprising a star-shaped oligomeric or polymeric scaffold comprising three to six branches, wherein each branch terminal comprises a photoreactive group able to undergo a reversible reaction upon stimulation with light.

2. The photoreactive component of claim 1, wherein each photoreactive group is a group able to undergo a reversible photo dimerization.

3. The photoreactive component of claim 1, wherein each photoreactive group is selected from the group consisting of a cinnamic acid ester compound, a cinnamyl acid ester compound, cinnamylacyl acid, ortho-substituted cinnamic acids, cinnamyloxysilanes, 1,3-diphenyl-2-propene-1-one and 4-methylcoumarin.

4. The photoreactive component of claim 1, wherein the scaffold is a polyalkylene glycol scaffold or a polyethylene glycol scaffold.

5. A polymeric photosensitive network comprising the photoreactive component of claim 1 and an amorphous polymer network physically admixed therewith, the amorphous polymer network comprising a matrix component, which is transparent for light and has elastomeric properties.

6. The photosensitive polymeric network of claim 5, wherein the matrix component is at least one of an acrylate material and a methacrylate material.

7. The photosensitive polymeric network of claim 6, wherein the matrix component is based on at least one of a $C_1$- to $C_6$-acrylate and a $C_1$- to $C_6$-methacrylate.

8. The photosensitive polymeric network of claim 7, wherein the matrix component is based on at least one selected of the group consisting of hydroxyethyl acrylate, hydroxypropyl methacrylate, hydroxypropyl acrylate, poly (ethylene glycol)methacrylate and n-butyl acrylate.

9. The photosensitive polymeric network of claim 8, wherein the matrix component is a co-polymer of n-butyl acrylate and hydroxyethyl methacrylate.

10. The photosensitive polymeric network of claim 9, wherein the co-polymer has a mol ratio of n-butyl acrylate to hydroxyethyl methacrylate within the range from 10:0.1 to 10:5.

11. The photosensitive polymeric network of claim 5, wherein the amorphous polymer network further comprises a crosslinking component which is at least one of a diacrylate compound and a dimethacrylate compound.

12. The photosensitive polymeric network of claim 11, wherein the crosslinking component is at least one selected from the group consisting of ethylene diacrylate, poly(oxyethylene)diacrylate, poly(propylene)diacrylate and poly(propylene glycol)dimethacrylate.

13. The photosensitive polymeric network of claim 5, wherein the polymeric network comprises an amorphous network and a photoreactive component, wherein the photoreactive component is able to undergo a reversible photodimerization as to form the inter-penetrating part of an inter-penetrating network.

14. The photoreactive component of claim 1, wherein the photoreactive group is able to undergo a reversible reaction upon stimulation with ultraviolet light.

* * * * *